United States Patent
Mihalef et al.

(10) Patent No.: US 8,965,084 B2
(45) Date of Patent: Feb. 24, 2015

(54) BLOOD FLOW COMPUTATION IN VESSELS WITH IMPLANTED DEVICES

(71) Applicants: Viorel Mihalef, Keasbey, NJ (US); Puneet Sharma, Rahway, NJ (US); Thomas Redel, Poxdorf (DE); Ali Kamen, Skillman, NJ (US)

(72) Inventors: Viorel Mihalef, Keasbey, NJ (US); Puneet Sharma, Rahway, NJ (US); Thomas Redel, Poxdorf (DE); Ali Kamen, Skillman, NJ (US)

(73) Assignee: Siemens Aktiengesellschaft, Munich (DE)

( * ) Notice: Subject to any disclaimer, the term of this patent is extended or adjusted under 35 U.S.C. 154(b) by 176 days.

(21) Appl. No.: 13/744,857

(22) Filed: Jan. 18, 2013

(65) Prior Publication Data
US 2013/0191100 A1    Jul. 25, 2013

Related U.S. Application Data

(60) Provisional application No. 61/588,389, filed on Jan. 19, 2012.

(51) Int. Cl.
| | |
|---|---|
| G06K 9/00 | (2006.01) |
| G06K 9/36 | (2006.01) |
| G06F 19/00 | (2011.01) |
| G06T 19/00 | (2011.01) |
| A61B 6/03 | (2006.01) |
| A61B 6/00 | (2006.01) |

(52) U.S. Cl.
CPC ............ *G06F 19/3437* (2013.01); *G06T 19/00* (2013.01); *G06T 2210/41* (2013.01); *A61B 6/032* (2013.01); *A61B 6/486* (2013.01); *A61B 6/504* (2013.01); *A61B 6/5217* (2013.01)
USPC .......................................... 382/128; 382/285

(58) Field of Classification Search
CPC ...... A61B 5/02007; A61B 6/504; A61B 8/06; A61B 2018/00875; G06F 19/3437; G06F 19/12; G06T 19/00; G06T 2210/41
USPC ........................................................... 703/11
See application file for complete search history.

(56) References Cited

U.S. PATENT DOCUMENTS

| | | | | |
|---|---|---|---|---|
| 8,485,829 | B2 * | 7/2013 | Cusano ........................ | 434/267 |
| 2008/0020362 | A1 * | 1/2008 | Cotin et al. .................. | 434/267 |
| 2012/0041318 | A1 * | 2/2012 | Taylor .......................... | 600/504 |
| 2013/0132054 | A1 * | 5/2013 | Sharma et al. ................ | 703/9 |

* cited by examiner

*Primary Examiner* — Amir Alavi
*Assistant Examiner* — Kenny Cese (57) ABSTRACT

A method for modeling blood flow through a flow diverter includes receiving a medical image containing blood vessels. Vessel geometry is extracted from the received medical image. Inlets and outlets are tagged within the extracted vessel geometry. A desired flow diverter is selected. A model of the selected flow diverter is generated within the imaged blood vessel, the model representing the flow diverter as a tube having a porous surface characterized by a viscous resistance and an inertial resistance. A course of blood flow though the flow diverter is predicted based on the generated model, the extracted vessel geometry, and the tagged inlets and outlets.

22 Claims, 5 Drawing Sheets

BLOOD FLOW COMPUTATION IN VESSELS WITH IMPLANTED DEVICES

CROSS-REFERENCE TO RELATED APPLICATION

The present application is based on provisional application Ser. No. 61/588,389, filed Jan. 19, 2012, the entire contents of which are herein incorporated by reference.

TECHNICAL FIELD

The present disclosure relates to fluid dynamics of blood flow in vessels and, more specifically, to computational fluid dynamics of blood flow in vessels with aneurysms fitted with flow diverters using immersed porous boundary approaches.

DISCUSSION OF THE RELATED ART

Intracranial aneurysms are bulges in the walls of blood vessels of the brain, most commonly found within the anterior cerebral artery. If left untreated, intracranial aneurysms may rupture and lead to subarachnoid hemorrhage (SAH), a condition that may be fatal.

Intracranial aneurysms may be treated by surgical intervention. One such approach is known as surgical clipping. Here a craniotomy may be performed to expose the aneurysm and the base of the aneurysm may be closed using a clip thereby blocking the flow of blood to the aneurysm.

An alternative approach for surgical intervention involves the insertion of coils to the site of the aneurism. The coils may be inserted though the circulatory system thereby providing a minimally invasive means of delivery. The coils may be constructed of metallic wires, for example, platinum, which may induce clotting to close off the aneurysm. Intracranial stent may also be deployed to support the coils. The stents may be flexible self-expanding porous tubular meshes made of stainless steel or other alloys such as Nitinol.

An alternative approach to the use of intracranial stents is the use of flow diverters. Flow diverters are also porous tubular meshes but they are characterized by the use of very thin wires, for example, on the order of 30 to 50 microns. The pores or windows created thereby may be on the order of 100 microns. Flow diverters may have either a single-layer or multi-layered structure. Flow diverters, unlike intracranial stents, may be used by themselves without the aid of coils.

Blood flow simulation can provide useful information to the clinician (neurologist) when done as a pre-planning activity before flow diverter deployment. Aneurismal flow can be modeled before the placement of the flow diverter for purposes such as determining an appropriate flow diverter to use, how it should be placed, and to project the likely consequences of its placement. Aneurismal flow can also be modeled after the placement of the flow diverter to monitor efficacy. Various techniques are in use for performing anerismal flow simulation. One such example is computational fluids dynamics (CFD). However, while these computational techniques may be well suited for simulating blood flow through intracranial stents, the significantly finer scale of flow diverters makes blood flow simulation substantially more difficult. In fact, a simulation of blood flow through a flow diverter may take days or even weeks to calculate.

SUMMARY

A method for modeling blood flow through a flow diverter includes receiving a medical image containing blood vessels. Vessel geometry is extracted from the received medical image. Inlets and outlets are tagged within the extracted vessel geometry. A desired flow diverter is selected. A model of the selected flow diverter is generated within the imaged blood vessel, the model representing the flow diverter as a tube having a porous surface characterized by a viscous resistance and an inertial resistance. A course of blood flow though the flow diverter is predicted based on the generated model, the extracted vessel geometry, and the tagged inlets and outlets.

Patient-specific flow data may be obtained from the received medical image and this patient-specific flow data may be used as boundary conductions for predicting the course of blood flow though the flow diverter.

The image of the blood vessel may be a Computer Tomography (CT) scan, a Magnetic Resonance Image (MI), or a Digital Subtraction Angiography (CSA) study showing an aneurysm and the flow diverter may be modeled within the extracted vessel geometry of the imaged blood vessel in a manner appropriate for treating the aneurysm.

The desired flow diverter may be automatically or semi-automatically selected based on the image of the blood vessel. The desired type of flow diverter may be manually selected by a user.

The desired flow diverter may be a SILK stent. The desired flow diverter may be an endovascular device made of nitinol with a dense strut network designed for the redirection of flow. The desired flow diverter may include a set of wires each having a diameter within the range of 0.01 mm to 0.10 mm.

The viscous resistance and the inertial resistance of the desired flow diverter may be know prior to selection. The viscous resistance and an inertial resistance of the selected flow diverter may be a function of the shape of the selected flow diverter when positioned the imaged blood vessel.

The viscous resistance and the inertial resistance of the selected flow diverter may each be represented by a matrix. The viscous resistance matrix and the inertial resistance matrix of the selected flow diverter may be calculated using the formula: $Mv=(k_1-k_2)(n \cdot v)n+k_2 v$ where $Mv$ represents a symmetric resistance linear operator for a given fluid velocity vector $v$, and $n$ represents a given point along the surface of the flow diverter.

In generating the model of the selected flow diverter within the imaged blood vessel, a resistance force of the selected flow diverter may be spread to a computational grid of the model using an immersed boundary method.

Predicting the course of blood flow through the flow diverter may include solving Navier-Stokes equations for the fluid path of the flow diverter using the viscous resistance and inertial resistance of the selected flow diverter.

The method may additionally include displaying the predicted blood flow to a user. The predicted blood flow may be used to characterize an efficacy of the selected flow diverter. The steps of selecting the desired flow diverter, generating the model, predicting the course of blood flow though the flow diverter, and characterizing flow diverter efficacy may be repeated for multiple flow diverters to determine a flow diverter from among the multiple flow diverters that produces a greatest efficacy from a clinical viewpoint.

A method for modeling blood flow through a flow diverter includes receiving an image of a blood vessel. Vessel geometry is extracted and inlets and outlets are tagged from the image. A desired flow diverter is selected from among a plurality of available flow diverters, each of which having a known viscous resistance matrix and an inertial resistance matrix. A model of the selected flow diverter within the imaged blood vessel is generated. The model represents the flow diverter as a tube having a porous surface characterized by the viscous resistance matrix and the inertial resistance corresponding to the selected flow diverter. A course of blood flow though the flow diverter is predicted based on the generated model. The predicted course of blood flow through the flow diverter is used to characterize an efficacy of the selected flow diverter.

A computer system includes a processor and a non-transitory, tangible, program storage medium, readable by the computer system, embodying a program of instructions executable by the processor to perform method steps for modeling blood flow through a flow diverter. The method includes receiving an image of a blood vessel including an aneurysm. Vessel geometry is extracted from the received medical image. A desired flow diverter is selected for treating the aneurism from among a plurality of available flow diverters, each of which having a known viscous resistance matrix and an inertial resistance matrix. A model of the selected flow diverter applied within the imaged blood vessel to treat the aneurysm is generated. The model represents the flow diverter as a tube having a porous surface characterized by the viscous resistance matrix and the inertial resistance corresponding to the selected flow diverter. A course of blood flow though the flow diverter is predicted based on the generated model and the extracted vessel geometry.

The viscous resistance matrix and the inertial resistance matrix of the selected flow diverter may be calculated using the formula: $Mv=(k_1-k_2)(n \cdot v)n+k_2 v$ where Mv represents a symmetric resistance linear operator for a given fluid velocity vector v, and n represents a given point along the surface of the flow diverter.

The desired flow diverter may be automatically selected based on the image of the blood vessel.

The predicted blood flow may be used to characterize an efficacy of the selected flow diverter and the steps of selecting the desired flow diverter, generating the model, predicting the course of blood flow though the flow diverter, and characterizing flow diverter efficacy may be repeated for multiple flow diverters to determine a flow diverter from among the multiple flow diverters that produces a greatest efficacy.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide an approach for performing blood flow simulation in the vicinity of an aneurysm with an implanted flow diverter. This aneurismal numerical flow simulation may be performed based on angiography data of the blood flow through the aneurysm and a geometric model of the flow diverter being used. Conventional approaches to aneurismal flow simulation may model each wire and pore of the flow simulator. However, because of the fine structure of these wires, full simulation may be exceptionally complex and may take weeks to perform.

Accordingly, rather than modeling each fine wire of the flow diverter, exemplary embodiments of the present invention may model the structure of the flow diverter as a single tubular structure comprised of a porous medium.

Figure 1:
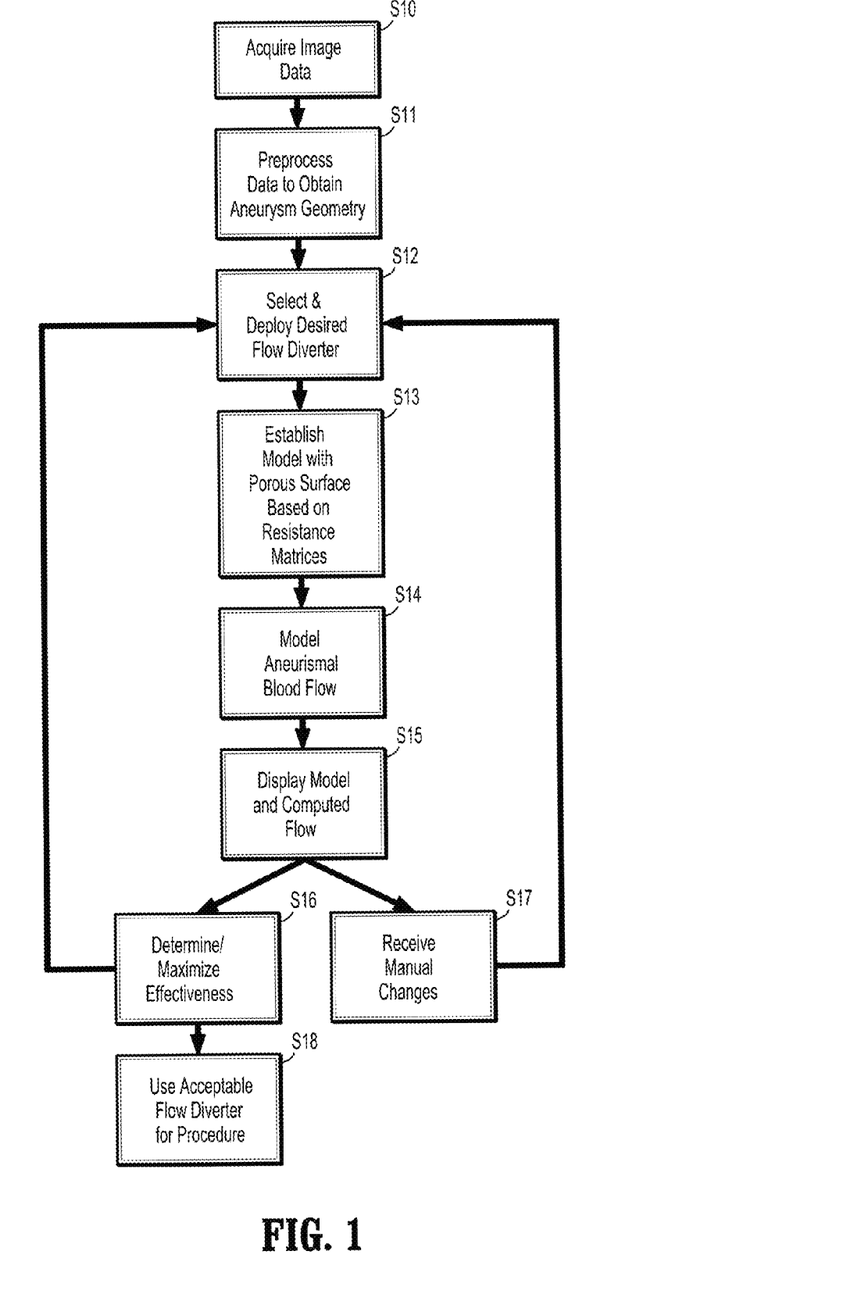
FIG. 1 is a flow chart illustrating an approach for performing computational fluid dynamics of blood flow in aneurysms with flow diverters using immersed porous boundary in accordance with exemplary embodiments of the present invention.

FIG. 1 is a flow chart illustrating an approach for performing computational fluid dynamics of blood flow in aneurysms with flow diverters using immersed porous boundary in accordance with exemplary embodiments of the present invention. First, image data may be acquired (Step S10). The image data may include CT data, MR data and/or DSA (Digital Subtraction Angiography) data may also be acquired. The imaging data may include an aneurysm such as an intracranial aneurysm. The angiography data may be acquired using an x-ray imager, fluoroscope, or CT scanner, for example, after a radiopaque contrast agent has been administered into a subject's blood stream. Next, the acquired image data may be preprocessed to extract the vessel geometry (Step S11). Preprocessing may be performed directly from the CT data, MR data, from DSA data or from other imaging modalities. This geometry is tagged with inlets and outlets, marking the way the blood enters and leaves the vessels. Angiography data can also provide patient specific boundary conditions that can be used by the numerical simulation engine, namely inlet and outlet velocity values. From these values one can estimate the pressure drop from inlet to outlets, and use the pressure values as boundary conditions.

Next, a desired flow diverter may be selected and the selected flow diverter may then be deployed virtually in the aneurysm vessel geometry (Step S12). In this way, the flow diverter may be modeled for the computation as an immersed porous boundary. This can be done semi-automatically, using either a fast energy minimizing method which requires only two clicks marking the beginning and end of the flow diverter, or by using a virtual deployment tool which takes into account the flow diverter mechanical deformation properties. The flow diverter may be selected in accordance with various requirements, for example, as defined by the nature of the aneurism. Selection of the desired flow diverter may be performed either manually or automatically, for example, based on the acquired angiography data. Computational fluid dynamics may thereafter be performed to model the blood flow in the presence of the flow diverter. This may be accomplished by determining one or more model parameters for the selected flow diverter and applying them to the computational flow model that includes a representation of the flow diverter as a tube having porous boundaries (Step S13). According to exemplary embodiments of the present invention, the model parameters may represent pressure losses with respect to velocities, due to frictional resistances within the flow diverter. The one or more model parameters may include, for example, resistance matrices modeling the viscous resistance and inertial resistance. The porosity of the flow diverter surface may be modeled using the determined one or more parameters.

Pressure losses due to frictional resistances may be characterized in terms of both hydraulic resistance and viscous resistance.

The fluid flow through the porous diverter may be modeled by the addition of a momentum source term to the standard Navier-Stokes equations that model viscous fluid flow. The source term may be composed of two parts accounting for the viscous momentum loss and inertial momentum loss. Together, these momentum source terms may comprise the model parameters for the selected flow diverter. The porous fluid flow equation may thereby be:

$$\rho\left(\frac{\partial u}{\partial t} + u \cdot \nabla u\right) = \nabla \cdot (-pI + \mu \nabla u) + S \qquad (1)$$

The porous source term may be defined as $S=-(\mu Au + \frac{1}{2}\rho|u|Cu$, where A and C are the inverse permeability and the inertial resistance tensors and/or matrices, respectively. A and C may be obtained either experimentally or numerically, for example, by imposing normal and tangential flow in "pill-boxes" to divert mesh and fitting $\Delta p = \alpha u + \beta u^2$. These terms may be non-homogenous diverter-specific matrices that take into account the spatial distribution of the directional viscous and inertial resistances. According to a simple example of a homogenous media, $$Au = \frac{1}{\alpha}u$$

and $Cu=C_2u$, with the constants being the permeability and the inertial resistance factor.

Here $\alpha$ is the permeability of the flow diverter surface, $C_2$ is the inertial resistance factor, u is the velocity, $\mu$ is the viscosity, and $\rho$ is the density.

The permeability and the inertial resistance factors are diverter-specific and may be determined and specified by the user before usage in the porous diverter solver. By default the resistance parameters may be set in accordance with Table 1 when using a SILK stent flow diverter such as pictured in FIG. 2.

Figure 2:
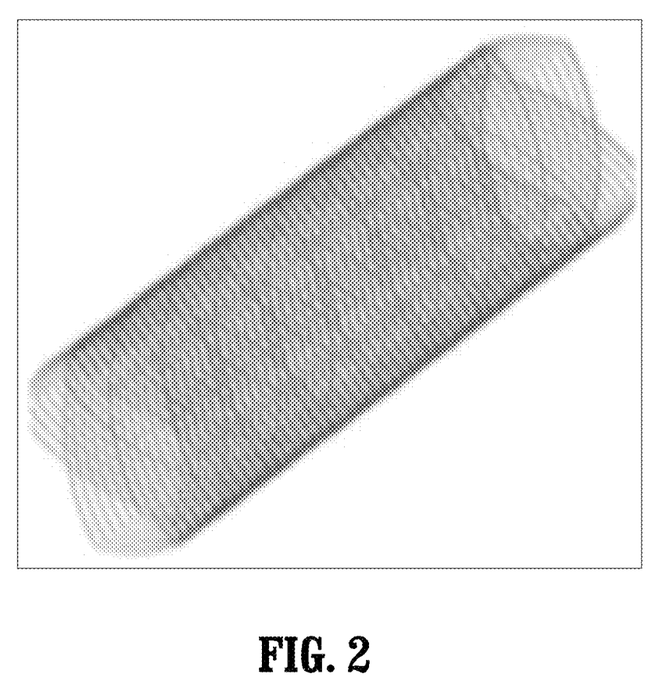
FIG. 2 is a model of a flow diverter used in conjunction with exemplary embodiments of the present invention.

The SILK stent flow diverter may be an endovascular device made of nitinol with a dense strut network designed for the redirection of flow. It may be composed of approximately 48 wires, 40 wires having a diameter of 0.03 mm and 8 having a diameter of 0.05 mm. However suitable flow diverters may include wires of any size, and in particular, wires with a diameter of between 0.01 mm to 0.10 mm.

TABLE 1

Viscous and inertial resistances of the SILK flow diverter.

| Porous medium parameters | Viscous resistance (linear) 1/a (1/mm2) | | Inertial resistance (quadratic) C2 (1/mm) | |
|---|---|---|---|---|
| | Tangential | Normal | Tangential | Normal |
| Shear and inertia driven flow models | 1700 | 890 | 4.7 | 8.7 |

Flow diverters may exhibit non-homogenous viscous and inertial resistances, dependent on the direction of the fluid flow. The resistance may be modeled by linear operators such that the resistance at a given point on the diverter is given both in the normal direction and in the tangential plane. For example, the resistance operators may have a given eigenvalue along the normal direction and another eigenvalue in any direction belonging to the tangent plane. Accordingly, the following formula may be used:

$$Mn=k_1n, \text{ and } Mt=k_2t, \qquad (2)$$

where n is the unit normal vector, t is any unit tangent vector, and M is the symmetric resistance linear operator. Here, $k_1$ and $k_2$ represent eigenvalue coefficients for permeability. For any fluid velocity vector v, unique splitting $v=v_n+v_T$ may be used and accordingly $Mv=Mv_n+Mv_T=k_1v_n+k_2v_T=k_1(n\cdot v)n + k_2(v-v_n)$. The final computation formula for the resistance matrices may be obtained by:

$$Mv=(k_1-k_2)(n\cdot v)n+k_2v \qquad (3)$$

The same formula may be obtained from (Eq. 2), by writing explicitly the formula for the symmetric resistance operator $M=SDS^t$ (with $S=[n \ t_1 \ t_2]$ and $D=\text{diag}(k_1, k_2, k_2)$ using the conventions from (Eq. 2).

For example, using the flow diverter parameters from Table 1, the viscous loss may be equal to $S_{viscous}=-\mu(-810(n\cdot u)n + 1700u)$ while the inertial loss may be equal to $S_{inertial}=-0.5\rho|u|(4(n\cdot u)n+4.7u)$.

After the resistance matrices for viscous resistance and inertial resistance have been calculated, anerismal blood flow though the selected flow diverter may be calculated using a Navier-Stokes solver (Step S14).

The matrices for viscous resistance and inertial resistance may be precalculated for each available flow diverter and stored in a database so that calculation of these parameters need not be performed at the time of the simulation.

To include the thin porous source term in the Navier-Stokes equations in a form appropriate for discretization, an approach similar to the immersed boundary method may be used. The blood flow may first be expressed by the equation:

$$S(x, t) = \int_D S(y, t)\delta(x-y)dy \qquad (4)$$

where $\delta$ is the three dimensional Dirac delta function, and D is the diverter set of points, t is time. The three-dimensional approximation to the delta function may be given by the product $\delta^3_h(x-y)=\delta^1_h(x^0-y^0)\delta^1_h(x^0-y^0)\delta^1_h(x^0-y^0)$ where $$\delta^1_h(x^0-y^0) = \frac{1}{h}\phi\left(\frac{x^0-y^0}{h}\right)$$

is an approximation to the 1-dimensional Dirac delta function. Following, given $r=(x^0-y^0)/h$ we choose the "3-cell" formula for the approximating function:

$$\phi(r) = \begin{cases} \frac{1}{6}(5-3|r|-\sqrt{1-3(1-|r|)^2}), & 0.5 \le |r| \le 1.5 \\ \frac{1}{3}(1+\sqrt{1-3r^2}), & |r| \le 0.5 \\ 0, & \text{otherwise} \end{cases} \qquad (5)$$

This function may be chosen with a support of (only) three mesh widths in each space direction due to the use of MAC (staggered) discretizations for the velocity and pressure variables. As shown by, this function is differentiable, with finite support, and it guarantees conservation of momentum and angular momentum when used in the spreading of an immersed boundary force to the Eulerian grid points.

Figure 3:
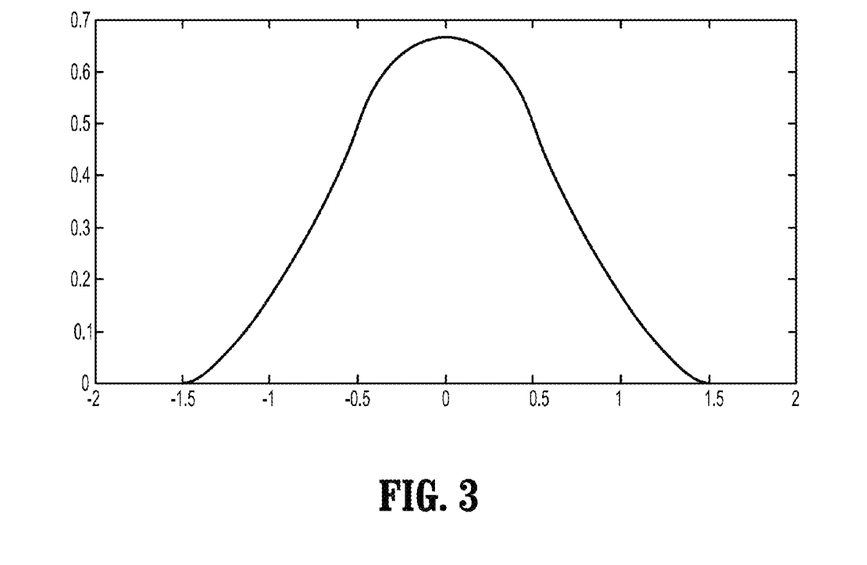
FIG. 3 is a graph illustrating an example of a three mesh width spreading profile in accordance with exemplary embodiments of the present invention.

FIG. 3 is a graph illustrating an example of a three mesh width spreading profile in accordance with exemplary embodiments of the present invention. For spreading the source term from the diverter surface to the computational grid points the integral $$S(x, t) = \int_D S(y, t)\delta(x - y)dy$$

may be evaluated. To evaluate the integral, the axial distances from the diverter surface to each computational point may be computed. This may be done, for example, by computing the Closest Point Transform (CPT).

The computation of the porous diverter source terms may plug directly into the CFD solver dedicated to brain aneurysm blood flow computation. The modified algorithm may be as follows:

1. Geometry preprocessing: given tagged STL triangular mesh (with separate tags for vessel inlet, wall, outlets and diverter) create signed distance function from vessel mesh, including distance function from diverter mesh. Tag computational grid points for Dirac delta.

2. Navier-Stokes solution step: (2.1) velocity advection, (2.2) velocity diffusion, (2.3) computation of porous momentum sink components at the tagged grid points, (2.4) pressure Poisson solution, and (2.5) velocity update.

The computation of the porous momentum terms may be performed directly on the MAC grid points that were tagged as "diverter influenced" computational points. These points may be the points touched by the support set of the Dirac delta. For any MAC grid velocity the corresponding velocity magnitude may be computed by averaging the centered velocities of the two adjacent cells.

Including the porous sink terms may lead to extra constraints on the time step. The new source terms lead to a new constraint on the time step in the case in which they reverse the velocity to a value larger in absolute value than its present value. For example, the Porous Sink CFL (PS-CFL) condition $$dt < \frac{dx}{\left|v_i - v_i\left(\frac{\mu}{\alpha} + \frac{C_2}{2}\rho|v|\right)\right|}$$

where $\alpha$ and $C_2$ are taken with their maximal values among the tangential and the normal ones, may be followed and this constraint on dt may be enforced when it is stronger than the CFL constraint. This may be the case when $$\frac{\mu}{\alpha} + \frac{C_2}{2}\rho|v| > 2.$$

This leads to a fastcheck condition that can be performed at the beginning of each time step in order to check if enforcing the PS-CFL is needed or not, for example, using the equation:

$$\max|v| > \frac{\left|4 - \frac{2\mu}{\alpha}\right|}{\rho C_2} \quad (6)$$

For example for standard blood viscosity and density parameters, the following relation may be obtained:

$$\max|v| > \frac{\left|4000 - \frac{8}{\alpha}\right|}{C_2} \quad (7)$$

In modeling the blood flow, various known parameters or estimated parameters may be used. For example, blood may be modeled as an incompressible Newtonian fluid with a density of 1.06 g cm$^{-3}$ and a viscosity of 4 mPa s. Vessel walls may be assumed to be rigid with a no slip boundary condition at the wall.

The flow may be computer either continuously or in time increments of, for example, 0.01 s for a cardiac cycle period of for example T–0.8 s.

After the blood flow has been calculated, the resulting blood flow model may be presented to a user (Step S15). Presentation of the blood flow may be in the form of data, a graph or a simulation, displayed in either 2D or 3D.

Figure 4:
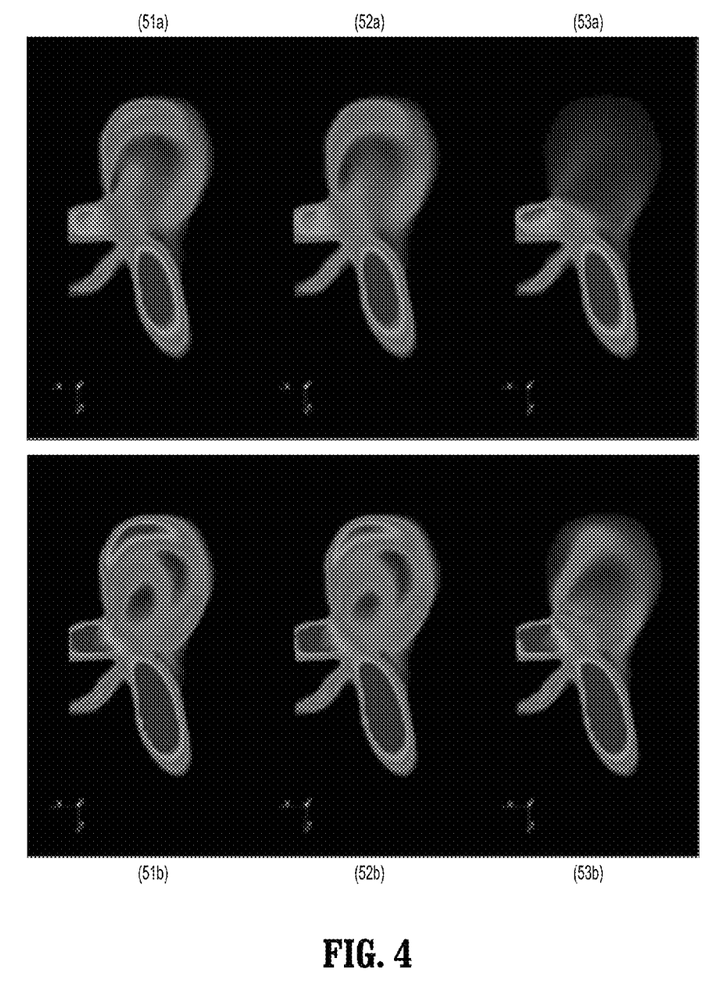
FIG. 4 is an illustration including a set of blood flow simulations in brain aneurysm as may be calculated in accordance with exemplary embodiments of the present invention.

FIG. 4 is an illustration including a set of blood flow simulations (including velocity magnitudes) in brain aneurysm. Simulations 51a and 51b show the flow of blood with no diverter. Simulations 52a and 52b show the flow of blood with a highly permeable diverter. Simulations 53a and 53b show the flow of blood with a reduced permeability diverter. Simulations 51a, 52a, and 53a are all simulations taken at time 0.5 s in a 0.72 s cardiac cycle. Simulations 51b, 52b, and 53b are all simulations taken at time 0.65 s in a 0.72 s cardiac cycle. Reduced circulation inside the aneurysm is shown to occur for the reduced permeability diverter.

In FIG. 4, simulations of aneurismal blood blow through various flow diverters are shown. The highly permeable diverter allows most of the flow to the aneurysm region while the reduced permeability diverter reduces drastically the flow circulation across the diverter.

The effectiveness of the chosen flow diverter may be automatically or manually determined based on the simulation results (Step S16). Where desired, this effectiveness score may be displayed to a user. The effectiveness score may be based, for example, upon the extent of simulated blood flow within the aneurysm. For example, higher scores may be provided for simulations that show less blood flow to the aneurysm.

After a flow diverter of a maximum effectiveness has been determined or a particular flow diverter has otherwise been shown to be suitable, the user may accept the flow diverter and the surgical intervention may be performed using the accepted flow diverter (Step S18).

The user may thereafter be presented with an opportunity to rerun the calculations using a different type of flow diverter, using a differently configured flow diverter or with any other changed parameter (Step S17). Alternatively, exemplary embodiments of the present invention may automatically rerun the simulation for various different flow diverters and/or flow diverter configurations until the effectiveness score has been maximized. Exemplary embodiments of the present invention may provide for reducing the computation time needed to perform the blood flow simulation. Accordingly, the user may be enabled to conduct an optimization process as outlined above within a reasonable amount of time.

Figure 5:
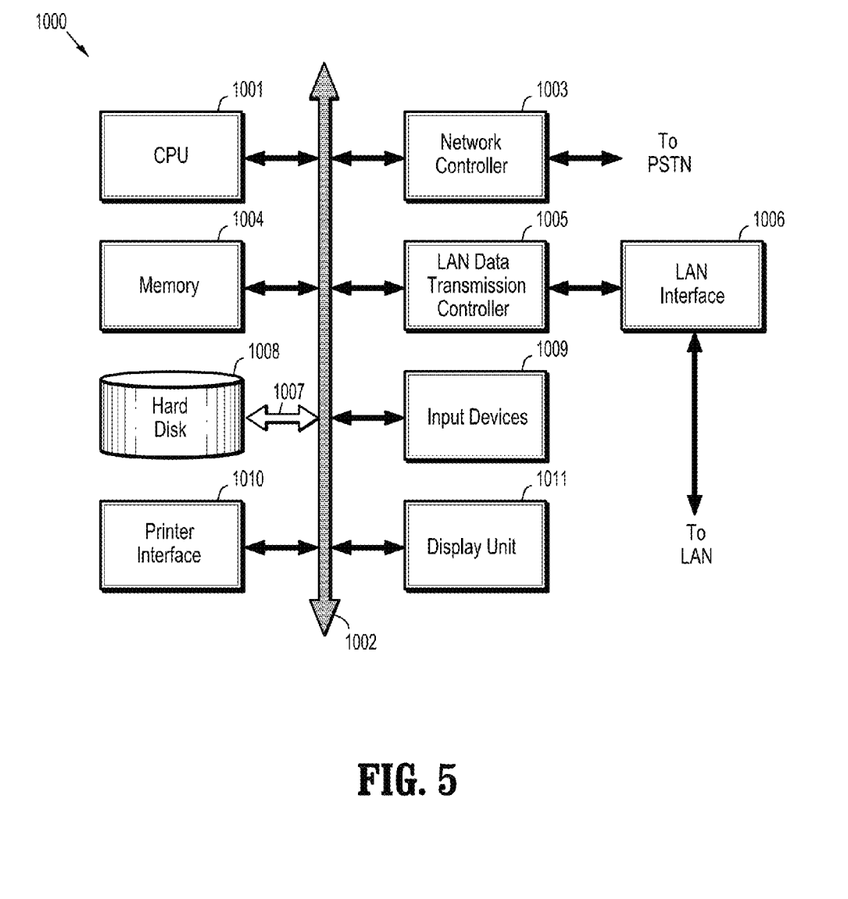
FIG. 5 shows an example of a computer system capable of implementing the method and apparatus according to embodiments of the present disclosure.

The blood flow simulation utilizing the techniques described in detail above may be performed using a computer system. FIG. 5 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for modeling blood flow through a flow diverter, comprising:
    receiving a medical image containing blood vessels;
    extracting vessel geometry from the received medical image;
    tagging inlets and outlets within the extracted vessel geometry;
    selecting a desired flow diverter;
    generating a model of the selected flow diverter within the imaged blood vessel, the model representing the flow diverter as a tube having a porous surface characterized by a viscous resistance and an inertial resistance; and
    predicting a course of blood flow though the flow diverter based on the generated model, the extracted vessel geometry, and the tagged inlets and outlets.

2. The method of claim 1, wherein patient-specific flow data is obtained from the received medical image and this patient-specific flow data is used as boundary conductions for predicting the course of blood flow though the flow diverter.

3. The method of claim 1, wherein the image of the blood vessel is a Computer Tomography (CT) scan, a Magnetic Resonance Image (MI), or a Digital Subtraction Angiography (CSA) study showing an aneurysm and the flow diverter is modeled within the extracted vessel geometry of the imaged blood vessel in a manner appropriate for treating the aneurysm.

4. The method of claim 1, wherein the desired flow diverter is automatically or semi-automatically selected based on the image of the blood vessel.

5. The method of claim 1, wherein the desired type of flow diverter is manually selected by a user.

6. The method of claim 1, wherein the desired flow diverter is a SILK stent.

7. The method of claim 1, wherein the desired flow diverter is an endovascular device made of nitinol with a dense strut network designed for the redirection of flow.

8. The method of claim 1, wherein the desired flow diverter comprises a set of wires each having a diameter within the range of 0.01 mm to 0.10 mm.

9. The method of claim 1, wherein the viscous resistance and the inertial resistance of the desired flow diverter is known prior to selection.

10. The method of claim 1, wherein the viscous resistance and an inertial resistance of the selected flow diverter is a function of the shape of the selected flow diverter when positioned the imaged blood vessel.

11. The method of claim 1, wherein the viscous resistance and the inertial resistance of the selected flow diverter are each represented by a matrix.

12. The method of claim 11, wherein the viscous resistance matrix and the inertial resistance matrix of the selected flow diverter are calculated using the formula: $Mv=(k_1-k_2)(nv)n+k_2v$ where My represents a symmetric resistance linear operator for a given fluid velocity vector v, and n represents a given point along the surface of the flow diverter.

13. The method of claim 1, wherein in generating the model of the selected flow diverter within the imaged blood vessel, a resistance force of the selected flow diverter is spread to a computational grid of the model using an immersed boundary method.

14. The method of claim 1, wherein predicting the course of blood flow through the flow diverter includes solving Navier-Stokes equations for the fluid path of the flow diverter using the viscous resistance and inertial resistance of the selected flow diverter.

15. The method of claim 1, additionally comprising displaying the predicted blood flow to a user.

16. The method of claim 1, wherein the predicted blood flow is used to characterize an efficacy of the selected flow diverter.

17. The method of claim 16, wherein the steps of selecting the desired flow diverter, generating the model, predicting the course of blood flow though the flow diverter, and characterizing flow diverter efficacy is repeated for multiple flow diverters to determine a flow diverter from among the multiple flow diverters that produces a greatest efficacy from a clinical viewpoint.

18. A method for modeling blood flow through a flow diverter, the method comprising:
    receiving an image of a blood vessel;
    extracting vessel geometry and tagging inlets and outlets from the image;
    selecting a desired flow diverter from among a plurality of available flow diverters, each of which having a known viscous resistance matrix and an inertial resistance matrix;
    generating a model of the selected flow diverter within the imaged blood vessel, the model representing the flow diverter as a tube having a porous surface characterized by the viscous resistance matrix and the inertial resistance matrix corresponding to the selected flow diverter;
    predicting a course of blood flow though the flow diverter based on the generated model; and
    using the predicted course of blood flow through the flow diverter to characterize an efficacy of the selected flow diverter.

19. A computer system comprising:
    a processor; and
    a non-transitory, tangible, program storage medium, readable by the computer system, embodying a program of instructions executable by the processor to perform method steps for modeling blood flow through a flow diverter, the method comprising:

receiving an image of a blood vessel including an aneurism;

extracting vessel geometry from the received medical image;

selecting a desired flow diverter for treating the aneurism from among a plurality of available flow diverters, each of which having a known viscous resistance matrix and an inertial resistance matrix;

generating a model of the selected flow diverter applied within the imaged blood vessel to treat the aneurysm, the model representing the flow diverter as a tube having a porous surface characterized by the viscous resistance matrix and the inertial resistance matrix corresponding to the selected flow diverter; and predicting a course of blood flow though the flow diverter based on the generated model and the extracted vessel geometry.

20. The computer system of claim 19, wherein the viscous resistance matrix and the inertial resistance matrix of the selected flow diverter are calculated using the formula: $Mv=(k_1-k_2)(nv)n+k_2v$ where My represents a symmetric resistance linear operator for a given fluid velocity vector v, and n represents a given point along the surface of the flow diverter.

21. The computer system of claim 19, wherein the desired flow diverter is automatically selected based on the image of the blood vessel.

22. The computer system of claim 19, wherein the predicted blood flow is used to characterize an efficacy of the selected flow diverter and the steps of selecting the desired flow diverter, generating the model, predicting the course of blood flow though the flow diverter, and characterizing flow diverter efficacy is repeated for multiple flow diverters to determine a flow diverter from among the multiple flow diverters that produces a greatest efficacy.

* * * * *